United States Patent [19]
Zimmer et al.

[11] Patent Number: 6,022,875
[45] Date of Patent: Feb. 8, 2000

[54] USE OF SUBSTITUTED 2,4-IMIDAZOLIDINEDIONE COMPOUNDS AS ANALGESICS

[75] Inventors: Oswald Zimmer, Wuerselen; Norma Selve, Aachen, both of Germany

[73] Assignee: Gruenenthal GmbH, Aachen, Germany

[21] Appl. No.: 09/126,753

[22] Filed: Jul. 31, 1998

[30] Foreign Application Priority Data

Jul. 31, 1997 [DE] Germany .................. 197 32 928

[51] Int. Cl.[7] .................................................. A01N 43/58
[52] U.S. Cl. .................... 514/252; 514/282; 514/341; 514/362; 514/363; 514/370; 514/380; 514/387; 514/389; 514/646
[58] Field of Search ..................... 514/252, 341, 514/362, 363, 370, 380, 387, 389, 282, 646

[56] References Cited

U.S. PATENT DOCUMENTS

| | | |
|---|---|---|
| 5,733,936 | 3/1998 | Buschmann et al. . |
| 5,811,582 | 9/1998 | Buschmann et al. . |

FOREIGN PATENT DOCUMENTS

| | | |
|---|---|---|
| 2188908 | 4/1997 | Canada . |
| 770613 | 5/1997 | European Pat. Off. . |
| 4426245A1 | 2/1996 | Germany . |
| 19540027A1 | 4/1997 | Germany . |
| 19609847A1 | 9/1997 | Germany . |
| WO92/07567 | 5/1992 | WIPO . |

OTHER PUBLICATIONS

Randall et al., Arch. int. pharmacodyn. CXI, No. 4, pp. 409–19 (1957).
Litchfield et al., J. Pharmacol, Exp Ther. 113: 96–99 (1949).
Dubuisson et al., Pain, 4: 161–74 (1977).
Hunskaar et al., Pain, 30: 103–14 (1987).
Witkin et al., J. Pharmacol. Exp. Ther. 133: 400–08 (1961).
Patent Abstracts of Japan, abstract of JP 55–051,068, 1980.
Patent abstracts of Japan, abstract of JP 09–176,131, 1997.
Satsangi et al., "1–(4–substituted–thiazol–2–yl) Hydantoins as Anti–Inflammatory and CNS–Active Agents". *Pharmazie* 38:341–2 (1983).

*Primary Examiner*—William R. A. Jarvis
*Attorney, Agent, or Firm*—Evenson, McKeown, Edwards & Lenahan, P.L.L.C.

[57] ABSTRACT

Disclosed in this invention is a method of analgesic treatment comprising administering an effective analgesic amount of a substituted 2,4-imidazolidinedione compound.

6 Claims, No Drawings

USE OF SUBSTITUTED 2,4-IMIDAZOLIDINEDIONE COMPOUNDS AS ANALGESICS

BACKGROUND OF THE INVENTION

This invention relates to the use of substituted 2,4-imidazolidinedione compounds for the production of pharmaceutical preparations for the treatment of pain.

Pain is a subjective sensory experience consisting of a sensory component and an affective component. The physiological aspects of the aetiology of pain comprise reception of any physical/chemical stimulus of a potentially tissue-threatening intensity by activation of the so-called nociceptors, specific uni- or polymodal nocisensors of high-threshold primary ascending neural pathways. When considering the pathophysiological aspects of the aetiology of pain, all the components of the nociceptive system may be altered: reception by nocisensors, transmission to the spinal level, perception, awareness and processing at the supraspinal level. Plastic changes or the development of chronic conditions may be brought about not only by disruption of the afferent system but also by disrupted perception and processing and disruption of the descending, controlling, endogenic pain-relieving system. In chronic or neuropathic pain, various phenomena occur including sensitisation of the nocisensors by endogenic or exogenic substances. In the event of persistent stimulation or disruption of the integrity of the nociceptor, not only secondary but also central sensitisation may occur at the spinal level. Such phenomena are known in particular in chronic inflammatory conditions, for example in rheumatoid arthritis. Inflammatory tissue hormones and transmitters (histamine, serotonin, prostaglandins, interleukin-1) secreted by local inflamed cells in the vicinity of the nocisensor may result in sensitisation of the nociceptors with a reduced threshold of stimulus and increased spontaneous activity, wherein persistent inflammation with constant stimuli ultimately results in the development of adaptive processes at the spinal and supraspinal levels.

Substituted 2,4-imidazolidinedione compounds and the immunomodulating action thereof are known from co-pending patent application no. 08/738,232, filed Oct. 25, 1996 (=DE19540027.5), the disclosure of which is incorporated herein by reference.

SUMMARY OF THE INVENTION

It has surprisingly now been found that these compounds additionally have an anti-nociceptive action which cannot be derived from the hitherto known immunomodulating and anti-vasculitic action.

The present invention accordingly relates to the use of substituted 2,4-imidazolidinedione compounds of the formula I

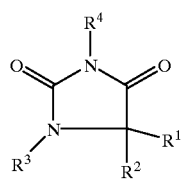

in which $R^1$ means $C_1$-$C_6$ alkyl or $C_{3-6}$ cycloalkyl and $R^2$ means $C_{1-6}$ alkyl, phenyl, —$(CH_2)_{1-3}$-phenyl or —$(CH_2)_{1-4}$—COOR$^5$ or $R^1$ and $R^2$ together mean —$(CH_2)_{4-6}$—, —$(CH_2)_2$—O—$(CH_2)_2$— or

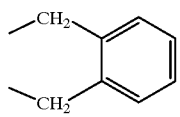

$R^3$ means H, $C_{1-5}$ alkyl or —$(CH_2)_{1-4}$—COOR$^5$, $R^4$ is a heteroaromatic group selected from the groups corresponding to the formulas

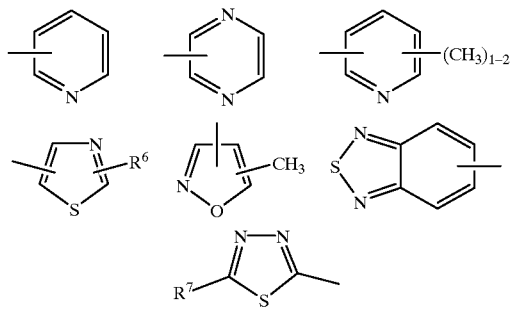

$R^5$ denotes $C_{1-3}$ alkyl, $R^6$ means H, $C_{1-4}$ alkyl, phenyl or benzyl and $R^7$ means H, $C_{1-4}$ alkyl or trifluoromethyl, for the treatment of pain and for the production of a pharmaceutical preparation for the treatment of pain.

Preferred substituted 2,4-imidazolidinedione compounds of the formula I are those in which $R^1$ denotes $C_{1-6}$ alkyl, $R^2$ denotes $C_{1-6}$ alkyl, phenyl or —$(CH_2)_{1-3}$-phenyl or $R^1$ and $R^2$ together denote —$(CH_2)_{4-6}$ or

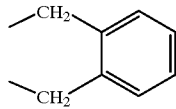

and $R^3$ denotes H or $C_{1-5}$ alkyl, and particularly preferred compounds of the formula I are those in which $R^1$ denotes $C_{1-4}$ alkyl, $R^2$ denotes $C_{3-5}$ alkyl or phenyl, or $R^1$ and $R^2$ together denote —$(CH_2)_5$— or

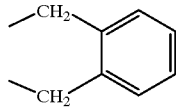

and $R^3$ denotes H or $C_{1-4}$ alkyl. It is particularly preferred to use substituted 2,4-imidazolidinedione compounds of the formula I in which $R^4$ means thiazol-2-yl or pyrazin-2-yl.

At least one substituted 2,4-imidazolidinedione compound of the formula I may be used as a sole active substance or in combination with one or more further active substances to produce an analgesic. Particularly suitable further active substances are selected from at least one of the groups opioids, tramadol material and non-opioid analgesics. Examples of opioids include morphine, hydromorphone, codeine, oxycodone, dihydrocodeine, dextropropoxyphene, buprenorphine, levomethadone, fentanyl, sufentanil, together with the pharmaceutical salts of the above-stated active substances. Tramadol material comprises tramadol [(1RS;2RS)-2-[(dimethylamino) methyl]-1-(3-methoxy-phenyl)cyclohexanol)], tramadol N-oxide, O-demethyl-tramadol, the tramadol derivatives disclosed in U.S. Pat. No. 5,733,936 (=DE19525137.7) and co-pending patent application Ser. Nos. 08/466,911, filed Jun. 6, 1995 (=DE4426245); 08/820,377, filed Mar. 12, 1997, now U.S. Pat. No. 5,811,582 (=DE19609847.5); and 09/038,033, filed Mar. 11, 1998 (=DE19710628.5), the disclosures of which are incorporated herein by reference, as well as the pharmaceutical salts of the aforementioned tramadol materials in racemic or enantiomeric form. Suitable non-opioid analgesics include, for example, acidic non-opioid carboxylic acids and carboxylic acid esters, such as salicylates, arylacetic acids and arylpropionic acids, for example acetylsalicylic acid, diclofenac, naproxen, ketoprofen and ibuprofen, acidic non-opioid heterocyclic keto-enol acids such as oxicams and pyrazolidinediones, for example piroxicam and tenoxicam, non-acidic, non-opioid anilines and pyrazolinones, for example paracetamol and metamizol, together with non-opioid pyridylcarbamates, for example flupirtine and benzoxazocines, for example nefopam.

In the use according to the invention of a substituted 2,4-imidazolidinedione compound of the formula I in combination with a further analgesic, the weight ratio of the two active substances is advantageously between 1:0.01 and 1:25.

The substances to be used according to the invention have a pain-relieving action irrespective of whether the pain is caused by inflammation. Furthermore the anti-nociceptive action of the substances to be used according to the invention does not correlate with TNFα inhibition. The anti-nociceptive action of the substituted 2,4-imidazolidinedione compounds of the formula I cannot be explained by known anti-nociceptive mechanisms, such as μ-opioid receptor agonism, monoaminergic re-uptake inhibition or by interaction with a receptor such as adenosine, α/β-adrenoceptor, GABA, galanin, glutamate/NMDA, histamine, somatostatin, tachykinin, VIP or NPY, or with one of the following channels, calcium, potassium, MAO, NO sythetase, protein kinase or enzyme/second messenger system. The pain-relieving action could conceivably be attributable to an interaction with endogenic NGF (nerve growth factor).

Substituted 2,4-imidazolidinedione compounds of the formula I are preferably used for the production of pharmaceutical preparations for the treatment of chronic pain conditions. Chronic pain conditions, i.e. chronic inflammatory and chronic neuropathic pain conditions, occur, for example, in rheumatism, secondary inflammatory osteoarthrosis, back pain, tension headaches, trauma, herpes zoster and trigeminal neuralgia.

Analgesics are produced by using the compounds to be used according to the invention together with carriers and/or adjuvants, such as excipients, fillers, solvents, diluents, colorants and/or binders. Selection of the auxiliary substances and the quantities to be used are dependent upon whether the analgesic to be produced is to be administered orally, intravenously, intraperitoneally, intradermally, intramuscularly, intranasally, buccally or locally. Preparations suitable for oral administration are those in the form of matrix tablets, coated tablets, multi-layer tablets, chewable tablets, sugar-coated tablets, capsules, pellets, drops, elixirs or syrups, those suitable for parenteral, topical and inhalatory application are in the form of solutions, suspensions, readily reconstitutable dry preparations and sprays. Compounds according to the invention in a depot in dissolved form, a backing film or a dressing, optionally with the addition of skin penetration promoters are examples of suitable percutaneous dosage forms. Delayed release of the compounds according to the invention may be achieved with oral or percutaneous preparations.

Each dose unit typically will contain 5 to 500 mg, preferably 10 to 200 mg, of at least one substituted 2,4-imidazolidinedione compound of the formula I.

EXAMPLES

The pain-relieving action of the substances to be used according to the invention was determined using three test models. The following substituted 2,4-imidazolidinedione compounds were produced in accordance with the process described in German patent application 19540027.5:

5-ethyl-5-phenyl-3-pyrazin-2-yl-2,4-imidazolidinedione (compound 1)

5-ethyl-5-phenyl-3-thiazol-2-yl-2,4-imidazolidinedione (compound 2)

3-thiazol-2-yl-1,3-diazaspiro[4.5]-2,4-decanedione (compound 3)

5-isobutyl-5-methyl-3-thiazol-2-yl-2,4-imidazolidinedione (compound 4)

3-thiazol-2-yl-1,3-diazaspiro[4.4]-2,4-benzononanedione (compound 5)

1-propyl-3-thiazol-2-yl-1,3-diazaspiro[4.5]-2,4-decanedione (compound 6)

5,5-dipropyl-3-thiazol-2-yl-2,4-imidazolidinedione (compound 7).

1. Randall-Selitto test

In order to determine in vivo anti-nociceptive action using the Randall-Selitto test (*Arch. Int. Pharmacodyn. Ther.* 111, 409 (1957)), oedema was induced in a rat's hind paw by injecting 0.1 ml of a 20% baker's yeast suspension, the oedema causing pronounced mechanohyperalgesia after 4 hours. Pain was then produced by applying increasing pressure (0–450 g/mm$^2$) with a punch (0.2 mm point diameter) on the rat's inflamed hind paw, the measured value being the pressure at which the rat produced a vocalisation reaction. Animals which produced no vocalisation up to the maximum permitted pressure were deemed to have complete pain relief. The test substances were administered intraperitoneally in a dose of 10 ml/kg 5 and 30 minutes before the Randall-Selitto measurement. The test results are stated as MPE (maximum possible effect) in % in accordance with the formula:

$$\frac{(V_t - V_0)}{(V_{max} - V_0)} \times 100$$

where $V_t$ is the value measured after administration of the test substance; $V_O$ is the value measured before administration of the test substance, and $V_{max}$ is the maximum value.

ED$_{50}$ values were calculated by linear regression and confidence intervals were calculated according to Litchfield & Wilcoxon (*J. Pharmacol. Exp. Ther.* 96, 99 (1949)).

| | Anti-nociceptive action in Randall-Selito test | | |
|---|---|---|---|
| | Dose | In vivo anti-nociceptive action | |
| Substance | mg/kg | MPE (%) | ED$_{50}$ (mg/kg) |
| Vehicle (aqueous carboxymethyl-cellulose suspension) | — | −15.6 ± 7.4 | |

-continued

Anti-nociceptive action in Randall-Selito test

| Substance | Dose mg/kg | In vivo anti-nociceptive action | |
|---|---|---|---|
| | | MPE (%) | $ED_{50}$ (mg/kg) |
| Comparison acetylsalicylic acid | 464 | 36.3 ± 8.2 | |
| Compound 1 | 100 | 10.2 ± 2.9 | |
| Compound 2 | | | 46.8 (37.8–58.2) |
| Compound 3 | | | 71.0 (58.6–87.2) |
| Compound 4 | 100 | 15.1 ± 7.0 | |
| Compound 5 | 100 | 35.0 ± 16.7 | |
| Compound 6 | | | 70.1 (55.9–90.9) |
| Compound 7 | | | 128.7 (97.5–152.6) |
| Vehicle (aqueous carboxymethyl-cellulose suspension) | | 2.3–19.8 | |
| Compound 3 | 46.4 | 14.5 ± 5.96 | |
| Tramadol | 2.15 | 13.5 ± 3.45 | |
| Compound 3 and Tramadol | 46.4 and 2.15 | 47.9 ± 8.77 | |
| Morphine | 1.46 | 12.0 ± 4.56 | |
| Compound 3 and Morphine | 46.4 and 1.46 | 23.3 ± 4.84 | |
| Metamizol | 21.5 | 5.1 ± 3.86 | |
| Compound 3 and Metamizol | 46.4 and 21.5 | 41.5 ± 11.52 | |
| Acetylsalicylic acid (ASA) | 464 | 1.1 ± 3.68 | |
| Compound 3 and ASA | 46.4 and 464 | 43.0 ± 8.28 | |
| Paracetamol | 464 | 19.7 ± 3.03 | |
| Compound 3 and Paracetamol | 46.4 and | 26.9 ± 6.45 | |

2. Formalin test

The formalin test (Pain 4, 161 (1977); Pain 30, 103 (1987)) was selected to test symptomatic efficacy in the event of chronic pain. In this test, once formalin had been injected into the hind paw of a rat or mouse, the animal's pain reaction was recorded by observation of its complex pattern of behavior and quantified using a scoring system when testing the efficacy of compound 3. This test is not limited to the detection of spinal flight reactions or individual, supraspinally controlled reactions, but instead records the complex changes in the animal's overall behavior.

For compound 3 in the rat, an $ED_{50}$ value of 35.6 mg/kg was determined for direct analgesic action and an $ED_{50}$ value of 33.3 mg/kg for analgesic inhibition in the second chronic phase and in the mouse an $ED_{50}$ value of 31.8 mg/kg was determined for direct analgesic action and an $ED_{50}$ value of 32.8 mg/kg for analgesic inhibition in the second ichronic phase.

3. Hot plate test

The spinal/supraspinal nociceptive reaction time in the hot plate test (J. Pharmacol. Exp. Ther. 133, 400 (1961)) was investigated to test action in the event of acute, non-inflammatory, thermal stimulus. For compound 3 in the mouse, an $ED_{50}$ value of approx. 100 mg/kg i.p. was determined for direct anti-thermohyperalgesic action.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations falling within the scope of the appended claims and equivalents thereof.

What is claimed is:

1. A method of treating pain in a mammal comprising administering to said mammal an effective analgesic amount of a substituted 2,4-imidazolidinedione compound corresponding to the formula I wherein $R^1$ denotes $C_1$-$C_6$ alkyl or $C_{3-6}$ cycloalkyl, and $R^2$ denotes $C_{1-6}$ alkyl, phenyl, —$(CH_2)_{1-3}$-phenyl or —$(CH_2)_{1-4}$—$COOR^5$, or $R^1$ and $R^2$ together denote —$(CH_2)_{4-6}$—, —$(CH_2)_2$—O—$(CH_2)_2$— or $R^3$ denotes H, $C_{1-5}$ alkyl or —$(CH_2)_{1-4}$—$COOR^5$, $R^4$ is a heteroaromatic group selected from groups corresponding to the formulas $R^5$ denotes $C_{1-3}$ alkyl, $R^6$ denotes H, $C_{1-4}$ alkyl, phenyl or benzyl, and $R^7$ denotes H, $C_{1-4}$ alkyl or trifluoromethyl.

2. A method according to claim 1, wherein $R^1$ denotes $C_{1-6}$ alkyl, $R^2$ denotes $C_{1-6}$ alkyl, phenyl or —$(CH_2)_{1-3}$-phenyl, or $R^1$ and $R^2$ together denote —$(CH_2)_{4-6}$—, or and $R^3$ denotes H or $C_{1-5}$ alkyl.

3. A method according to claim 2, wherein $R^1$ denotes $C_{1-4}$ alkyl, $R^2$ denotes $C_{3-5}$ alkyl or phenyl, or $R^1$ and $R^2$ together denote —$(CH_2)_5$—, or

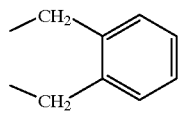

and $R^3$ denotes H or $C_{1-4}$ alkyl.

4. A method according to claim 1, wherein $R^4$ denotes thiazol-2-yl or pyrazin-2-yl.

5. A method according to claim 1, wherein said substituted 2,4-imidazolidinedione is administered in combination with at least one active substance selected from the group consisting of opioids, tramadol material and non-opioid analgesics.

6. A method according to claim 1, wherein said mammal is a mammal suffering from chronic pain.

* * * * *